US007435260B2

(12) United States Patent
Ferree

(10) Patent No.: US 7,435,260 B2
(45) Date of Patent: Oct. 14, 2008

(54) USE OF MORPHOGENETIC PROTEINS TO TREAT HUMAN DISC DISEASE

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 133 days.

(21) Appl. No.: 10/876,792

(22) Filed: Jun. 25, 2004

(65) Prior Publication Data

US 2004/0230310 A1 Nov. 18, 2004

Related U.S. Application Data

(63) Continuation-in-part of application No. 10/171,283, filed on Jun. 13, 2002, now Pat. No. 6,755,863, which is a continuation-in-part of application No. 09/688,716, filed on Oct. 16, 2000, now Pat. No. 6,454,804, which is a continuation-in-part of application No. 09/638,726, filed on Aug. 14, 2000, now Pat. No. 6,340,369, and a continuation-in-part of application No. 09/415,382, filed on Oct. 8, 1999, now Pat. No. 6,419,704.

(60) Provisional application No. 60/159,488, filed on Oct. 14, 1999, provisional application No. 60/148,913, filed on Aug. 13, 1999.

(51) Int. Cl.
*A61F 2/44* (2006.01)
(52) U.S. Cl. ................................. 623/17.11
(58) Field of Classification Search ... 623/17.11–17.16, 623/925; 606/91
See application file for complete search history.

(56) References Cited

U.S. PATENT DOCUMENTS

| | | | | |
|---|---|---|---|---|
| 2,677,369 A | 5/1954 | Knowles | ...................... | 128/92 |
| 3,366,975 A | 2/1968 | Pangman | ........................ | 3/36 |
| 3,426,364 A | 2/1969 | Lumb | ............................ | 3/1 |
| 3,551,560 A | 12/1970 | Thiele | ......................... | 424/95 |
| 3,593,342 A | 7/1971 | Niebauer | ........................... | 3/1 |
| 3,648,294 A | 3/1972 | Shahrestani | ........................ | 3/1 |
| 3,855,638 A | 12/1974 | Pilliar | .............................. | 3/1 |
| 3,867,728 A | 2/1975 | Substad et al. | ..................... | 3/1 |
| 3,875,595 A | 4/1975 | Froning | .............................. | 3/1 |
| 3,883,902 A | 5/1975 | Lynch | ............................. | 3/36 |
| 4,229,839 A | 10/1980 | Schwemmer | ................. | 3/1.91 |
| 4,294,753 A * | 10/1981 | Urist | ........................... | 530/395 |
| 4,309,777 A | 1/1982 | Patil | ............................. | 3/1.91 |
| 4,349,921 A | 9/1982 | Kuntz | ................................ | 3/1 |
| 4,663,358 A | 5/1987 | Hyon et al. | .................... | 521/64 |
| 4,707,872 A | 11/1987 | Hessel | ............................ | 5/451 |
| 4,714,469 A | 12/1987 | Kenna | ......................... | 623/17 |
| 4,759,766 A | 7/1988 | Buettner-Janz et al. | ........ | 623/17 |
| 4,772,287 A | 9/1988 | Ray et al. | ...................... | 623/17 |
| 4,801,299 A | 1/1989 | Brendel et al. | ........... | 623/16.11 |
| 4,863,477 A | 9/1989 | Monson | ....................... | 623/17 |
| 4,874,389 A | 10/1989 | Downey | ....................... | 623/17 |
| 4,904,260 A | 2/1990 | Ray et al. | ...................... | 623/17 |
| 4,911,718 A | 3/1990 | Lee et al. | ...................... | 623/17 |
| 4,917,704 A | 4/1990 | Frey et al. | ..................... | 623/17 |
| 4,932,969 A | 6/1990 | Frey et al. | ..................... | 623/17 |
| 4,946,378 A | 8/1990 | Hirayama et al. | ............. | 623/17 |
| 5,002,576 A | 3/1991 | Fuhrmann et al. | ............. | 623/17 |
| 5,047,055 A | 9/1991 | Bao et al. | ...................... | 623/17 |
| 5,071,437 A | 12/1991 | Steffee | ......................... | 623/17 |
| 5,108,438 A | 4/1992 | Stone | ........................... | 623/17 |
| 5,123,926 A | 6/1992 | Pisharodi | ...................... | 623/17 |
| 5,171,280 A | 12/1992 | Baumgartner | ................ | 623/17 |
| 5,171,281 A | 12/1992 | Parsons et al. | ................. | 623/17 |
| 5,192,326 A | 3/1993 | Bao et al. | ...................... | 623/17 |
| 5,246,458 A | 9/1993 | Graham | ........................ | 623/17 |
| 5,258,031 A | 11/1993 | Salib et al. | ..................... | 623/17 |
| 5,258,043 A | 11/1993 | Stone | ........................... | 623/66 |
| 5,314,477 A | 5/1994 | Marnay | ........................ | 623/17 |
| 5,320,644 A | 6/1994 | Baumgartner | ................ | 623/17 |
| 5,370,697 A | 12/1994 | Baumgartner | ................ | 623/17 |
| 5,375,823 A | 12/1994 | Navas | ........................... | 267/17 |
| 5,401,269 A | 3/1995 | Buttner-Janz et al. | ......... | 623/17 |
| 5,425,773 A | 6/1995 | Boyd et al. | .................... | 623/17 |

(Continued)

OTHER PUBLICATIONS

Carriers That Concentrate Native Bone Morpohogenetic Protein in Vivo K. De Groot, Ph.D. Tissue Engineering vol. 4, No. 4, 1998.*

(Continued)

*Primary Examiner*—Suzette J Gherbi
(74) *Attorney, Agent, or Firm*—Gifford, Krass, Sprinkle, Anderson & Citkowski, P.C.

(57) ABSTRACT

Bone morphogenetic proteins (BMPs) are introduced into an affected intervertebral disc without the inclusion of disc cells. The inventions applies to all known and yet-to-be developed or discovered BMPs, including BMP-1, -2, -3, -4, -5, -6, -7, -8, -9, -10, . . . BMPn. The BMP(s) may be obtained from natural and/or recombinant sources. The BMP(s) may be introduced using any surgical technique, including percutaneous or laparoscopic approaches. As one delivery mechanism, a passageway may be formed through the annulus, with the substances then being introduced through the passageway. Alternatively, a carrier may be sewn or otherwise adhered to the inside or outside of the existing annulus using standard surgical procedures. Additional therapeutic substances such as culture medium, growth factors, differentiation factors, hydrogels, polymers, antibiotics, anti-inflammatory medications, or immunosuppressive medications could be introduced in conjunction with the BMP(s).

14 Claims, No Drawings

U.S. PATENT DOCUMENTS

| | | | | |
|---|---|---|---|---|
| 5,441,508 | A | 8/1995 | Gazielly et al. | 606/151 |
| 5,458,642 | A | 10/1995 | Beer et al. | 623/17 |
| 5,464,439 | A | 11/1995 | Gendler | 623/16.11 |
| 5,507,813 | A * | 4/1996 | Dowd et al. | 623/23.63 |
| 5,514,180 | A | 5/1996 | Heggeness et al. | 623/17.11 |
| 5,534,028 | A | 7/1996 | Bao et al. | 623/17 |
| 5,534,030 | A | 7/1996 | Navarro et al. | 623/17 |
| 5,545,229 | A | 8/1996 | Parsons et al. | 623/17.11 |
| 5,556,431 | A | 9/1996 | Buttner-Janz | 623/17 |
| 5,609,635 | A | 3/1997 | Michelson | 623/17 |
| 5,645,596 | A | 7/1997 | Kim et al. | 623/17 |
| 5,645,597 | A | 7/1997 | Krapiva | 623/17 |
| 5,674,294 | A | 10/1997 | Bainville et al. | 623/17 |
| 5,674,296 | A | 10/1997 | Bryan et al. | 623/17 |
| 5,683,465 | A | 11/1997 | Shinn et al. | 623/17 |
| 5,702,450 | A | 12/1997 | Bisserie | 623/17 |
| 5,711,960 | A | 1/1998 | Shikinami | 424/426 |
| 5,716,416 | A | 2/1998 | Lin | 623/17 |
| 5,782,830 | A * | 7/1998 | Farris | 606/61 |
| 5,800,549 | A | 9/1998 | Bao et al. | 623/17 |
| 5,824,093 | A | 10/1998 | Ray et al. | 623/17 |
| 5,824,094 | A | 10/1998 | Serhan et al. | 623/17 |
| 5,865,845 | A | 2/1999 | Thalgott | 623/17 |
| 5,865,846 | A | 2/1999 | Bryan et al. | 623/17 |
| 5,888,226 | A | 3/1999 | Rogozinski | 623/17 |
| 5,893,889 | A | 4/1999 | Harrington | 623/17 |
| 5,899,941 | A | 5/1999 | Nishijima et al. | 623/17 |
| 5,928,284 | A | 7/1999 | Mehdizadeh | 623/17 |
| 5,964,807 | A | 10/1999 | Gan et al. | 623/17.11 |
| 5,972,368 | A * | 10/1999 | McKay | 424/423 |
| 5,976,186 | A | 11/1999 | Bao et al. | 623/17.16 |
| 5,980,504 | A * | 11/1999 | Sharkey et al. | 604/510 |
| 6,022,376 | A | 2/2000 | Assell et al. | 623/17.16 |
| 6,090,112 | A | 7/2000 | Zucherman et al. | 606/61 |
| 6,110,210 | A | 8/2000 | Norton et al. | 623/17.16 |
| 6,113,639 | A | 9/2000 | Ray et al. | 623/17.16 |
| 6,132,465 | A | 10/2000 | Ray et al. | 623/17.16 |
| 6,146,420 | A | 11/2000 | McKay | 623/17.11 |
| 6,187,048 | B1 | 2/2001 | Milner et al. | 623/17.12 |
| 6,224,630 | B1 * | 5/2001 | Bao et al. | 623/17.16 |
| 6,231,615 | B1 | 5/2001 | Preissman | 623/23.73 |
| 6,245,107 | B1 | 6/2001 | Ferree | 623/17.11 |
| 6,332,779 | B1 | 12/2001 | Boyce et al. | 433/215 |
| 6,340,369 | B1 | 1/2002 | Ferree | 623/17.11 |
| 6,344,058 | B1 | 2/2002 | Ferree | |
| 6,352,557 | B1 | 3/2002 | Ferree | |
| 6,371,988 | B1 * | 4/2002 | Pafford et al. | 623/17.11 |
| 6,419,702 | B1 | 7/2002 | Ferree | |
| 6,423,095 | B1 * | 7/2002 | Van Hoeck et al. | 623/17.16 |
| 6,428,576 | B1 * | 8/2002 | Haldimann | 623/17.16 |
| 6,454,804 | B1 | 9/2002 | Ferree | |
| 6,558,390 | B2 * | 5/2003 | Cragg | 606/80 |
| 6,620,196 | B1 * | 9/2003 | Trieu | 623/17.16 |
| 6,645,247 | B2 | 11/2003 | Ferree | |
| 6,648,918 | B2 | 11/2003 | Ferree | |
| 6,648,919 | B2 | 11/2003 | Ferree | |
| 6,648,920 | B2 | 11/2003 | Ferree | |
| 6,685,695 | B2 | 2/2004 | Ferree | |
| 6,755,863 | B2 | 6/2004 | Ferree | |
| 6,793,677 | B2 | 9/2004 | Ferree | |
| 2001/0024823 | A1 | 9/2001 | Vulkicevic et al. | 435/325 |
| 2002/0082697 | A1 * | 6/2002 | Damien | 623/17.16 |
| 2003/0100108 | A1 | 5/2003 | Altaman et al. | 435/395 |
| 2003/0144197 | A1 | 7/2003 | Zheng et al. | 514/12 |
| 2003/0212456 | A1 | 11/2003 | Lipschitz et al. | 623/13.17 |
| 2003/0215426 | A1 | 11/2003 | French et al. | 424/93.7 |
| 2003/0228292 | A1 | 12/2003 | Gazit et al. | 424/93.21 |
| 2004/0054414 | A1 * | 3/2004 | Trieu et al. | 623/17.16 |
| 2004/0062753 | A1 | 4/2004 | Rezania et al. | 424/93.7 |
| 2004/0064192 | A1 | 4/2004 | Bubb | 623/23.5 |
| 2004/0220101 | A1 | 11/2004 | Ferree | |
| 2004/0220102 | A1 | 11/2004 | Ferree | |
| 2004/0230390 | A1 * | 11/2004 | DiMauro et al. | 623/17.12 |
| 2004/0236327 | A1 * | 11/2004 | Paul et al. | 606/61 |
| 2004/0236328 | A1 * | 11/2004 | Paul et al. | 606/61 |
| 2004/0244806 | A1 | 12/2004 | Ferree | |
| 2005/0119754 | A1 * | 6/2005 | Trieu et al. | 623/17.16 |
| 2008/0014179 | A1 | 1/2008 | Ferree | |

OTHER PUBLICATIONS

Carriers That Concentrate Native Bone Morphogenetic Protein in Vivo; K. De Groot, Ph.D Tissue Engineering vol. 4, Nov. 4, 1998.*

Proceedings 14th Annual Meeting North American Spine Society, Oct. 1999.

Proceedings 13th Annual Meeting North American Spine Society, Oct. 1998.

S. Breit, S. Wahl; "TGF-β and Related Cytokines in Inflammation," 2001.

S. Vukicevic, K. Sampath; "Bone Morphogenetic Proteins," 2002.

S. Yoon, K. Kim, J. Li, J. Park, T. Akamaru, W. Elmer, W. Hutton; "The Effect of Bone Morphogenetic Protein-2 on Rat Intervertebral Disc Cells in Vitro," SPINE, vol. 28, No. 16, pp. 1173-1780.

Padgett, et al.; "Human BMP Sequences Can Confer Normal Dorsal-Ventral Patterning in the Drosophilia Embryo," Proc. Natl. Acad. Sci., 90, 2905-2909.

Paramore, C. et al.; "The Safety of OP-1 for Lumbar Fusion with Compression—a Canine Study," Neurosurgery, vol. 44, No. 5, May 1999, pp. 1151-1155.

D. Kim, S. Moon, H. Kim, U. Kwon, M. Park, K. Han, S. Hahn, H. Lee, "Bone Morphogenetic Protein-2 Facilities Expression of Chondrogenic, not Osteogenic, Phenotype of Human Intervertebral Disc Cells," SPINE, vol. 28, No. 24, pp. 2679-2684.

T. Gründer, C. Gaissmaier, J. Fritz, R. Stoop, P. Hortschansky, J. Mollenhauer, W. Aicher, "Bone morphogenetic protein (BMP)-2 enhances the expression of type II collagen and aggrecan in chondrocytes embedded in alginate beads," OsteoArthritis and Cartilage, 2004, 12, pp. 559-567.

M. Kawakami, H. Hashizume, T. Matsumoto, Y. Enyo, M. Okada, M. Yoshida, Safety of Epidural Administration of Osteogenic Protein-1 (OP-1/BMP-7), SPINE, vol. 32, No. 13, pp. 1388-1393.

Masuda, Y. Imai, M. Okuma, C. Muehleman, K. Nakagawa, K. Akeda, E. Thonar, G. Andersson, H. An, "Osteogenic Protein-1 Injection into a Degenerated Disc Induces the Restoration of Disc Height and Structural Changes in the Rabbit Anular Puncture Model," SPINE, vol. 31, No. 7, pp. 742-754.

* cited by examiner

USE OF MORPHOGENETIC PROTEINS TO TREAT HUMAN DISC DISEASE

REFERENCE TO RELATED APPLICATIONS

This application is a continuation-in-part of U.S. patent application Ser. No. 10/171,283, filed Jun. 13, 2002, now U.S. Pat. No. 6,755,863, which is a continuation-in-part of U.S. patent application Ser. No. 09/688,716, filed Oct. 16, 2000, now U.S. Pat. No. 6,454,804.

U.S. Pat. No. 6,454,804 claims priority from U.S. Provisional Patent Application Ser. No. 60/159,488, filed Oct. 14, 1999, and is a continuation-in-part of U.S. patent application Ser. No. 09/638,726, filed Aug. 14, 2000, now U.S. Pat. No. 6,340,369; and U.S. patent application Ser. No. 09/415,382, filed Oct. 8, 1999, now U.S. Pat. No. 6,419,704.

U.S. Pat. No. 6,340,369 claims priority from U.S. Provisional Patent Application Ser. No. 60/148,913, filed Aug. 13, 1999.

The entire content of each application and patent are incorporated herein by reference.

FIELD OF THE INVENTION

This invention relates generally to treating human disc disease, and more particularly, to the use of biological substances in conjunction with such treatments.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15-25 lamellae around the nucleus pulposus. The fibers in the lamellae alternate their direction of orientation by 30 degrees between each-band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation.

To date, the treatment of tears or defects of the annulus fibrosis has relied for the most part on eliminating the defective disc or disc function. This may be accomplished by fusing the vertebra on either side of the disc. In terms of replacement, prior-art techniques replace either the nucleus or the nucleus and annulus functions. My U.S. Pat. No. 6,245,107, and Patent Cooperation Treaty Application Ser. No. PCT/US/14708 describe methods and devices to occlude annular defects.

SUMMARY OF THE INVENTION

Certain of my co-pending patent applications and issued patents referenced above disclose the repair of tissues and organs by adding live cells to the extracellular matrix of tissues or organs harvested to recently deceased human or animals. For example, with respect to intervertebral disc repair, fibrocytes, annulus fibrosis cells, cells that differentiate into annulus fibrosis cells, or cells that function like annulus fibrosis cells are harvested and combined with the extracellular matrix of the annulus fibrosis from a recently deceased human or animal to produce an engineered annulus fibrosis.

My issued U.S. Pat. No. 6,340,369, for example, discloses techniques whereby cultured cells are injected into an affected intervertebral disc. In the preferred embodiment, a transplanted nucleus is added to the patient's nucleus pulposus. Additional therapeutic substances may be added to the transplanted nucleus. For example, resorbable culture medium, tissue growth or differentiation factors (recombinant generated morphogenetic proteins (including BMPs), PDGF, TGF-.beta., EGF/TGF-.alpha., IGF-I, .beta.FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immuno-suppressive medications, etc. could be beneficial.

This invention extends these teachings through the introduction of substances, including the above-listed factors, into an affected disc without the inclusion of disc cells. In the preferred embodiments, bone morphogenetic proteins (BMPs), are introduced into an affected intervertebral disc without the inclusion of disc cells. The inventions applies to all known and yet-to-be developed or discovered BMPs, including BMP-1, -2, -3, -4, -5, -6, -7, -8, -9, -10, . . . BMPn. The BMP(s) may be obtained from natural and/or recombinant sources.

The BMP(s) may be introduced using any surgical technique, including percutaneous or laparoscopic approaches. As one delivery mechanism, a passageway may be formed through the annulus, with the substances then being introduced through the passageway. Alternatively, a carrier may be sewn or otherwise adhered to the inside or outside of the existing annulus using standard surgical procedures.

Additional therapeutic substances such as culture medium, growth factors, differentiation factors, hydrogels, polymers, antibiotics, anti-inflammatory medications, or immunosuppressive medications could be introduced in conjunction with the BMP(s).

DETAILED DESCRIPTION OF THE INVENTION

This invention resides in the introduction of substances, particularly bone morphogenetic proteins (BMPs), into an affected intervertebral disc without the inclusion of disc cells. The inventions applies to all known and yet-to-be developed or discovered BMPs, including BMP-1, -2, -3, -4, -5, -6, -7, -8, -9, -10, . . . BMPn. The BMP(s) maybe obtained from natural and/or recombinant sources.

Submitted with this application are references (scientific papers) that teach dosages and sources of the BMPs. The content of each of these references is incorporated herein by reference. These papers describe the use of BMPs in humans and animals to grow bone and articular cartilage. Others include summary BMP articles and articles that describe the effects of BMP on disc cells.

Applicable BMPs are becoming, increasingly commercially available. For example, rhBMP-2 may be obtained from Medtronic Sofamor Danek, Memphis Tenn. (known as INFUSE). Medtronic obtains the BMP from Genetics Institute, Cambridge Mass.

The substances may be introduced using any surgical technique, including percutaneous or laparoscopic approaches. As one delivery mechanism, a passageway may be formed through the annulus, with the substances then being introduced through the passageway. Alternatively, a carrier may be sewn or otherwise adhered to the inside or outside of the existing annulus using standard surgical procedures.

As one specific example, a sponge soaked with BMP-2 (or BMP-n) may be inserted into a disc to treat degenerative disc disease. For example, an absorbable collagen sponge, available from Integra Life Sciences, Plainsboro, N.J., could be soaked in a 1.5 mg rhBMP-2/ml sterile saline solution (available from Medtronic Sofamor Danek, Memphis, Tenn.) for 15 minutes before inserting the BMP impregnated sponge into the disc. Other doses of BMP would be acceptable; for example, doses from 0.04 micrograms to 32 mg of BMP, or higher or lower, could be used.

Other synthetic and natural carriers are acceptable, such as a polyactic/polyglycolic acid sponge. Examples include natural polymers of collagen, hyaluronans, chitosan, alignate, and other animal or plant-derived polysaccharides. Examples of synthetic polymers include poly(alpha-hydroxy acids) such as polylactide, polyglycolide, and their copolymers, polyanhydrides, polyphosphazenes, polypropylene fumarate, polyethylene glycol-PLA, poloxamers, and polyphosphate polymers.

Composites of natural materials, synthetic materials, or natural and synthetic impregnated materials could also be used as carriers. For example, composites of hyaluronan-impregnated PLA sponges, collagen-PLG-alginate, and PLGA-gelatin could be used. Alternatively, a slurry of the BMP, with or without a carrier, could be injected into the disc. As a further alternative, the BMP-2 or BMP-n could be inserted into a surgically created hole in the disc, or could be continuously infused from a pump. Pumps with remote reservoirs are well known to those skilled in the art.

I claim:

1. A method treating human disc disease, comprising the steps of:
   providing a slurry of a dose of a bone morphogenetic protein (BMP) and a carrier; and
   introducing the slurry into an intervertebral disc through a passageway formed in an annulus of the vertebral disc.

2. The method of claim 1, further including the step of introducing the BMP through a percutaneous or laparoscopic procedure.

3. The method of claim 1, further including the step of adding one or more therapeutic substances to the dose of a BMP.

4. The method of claim 3, wherein the therapeutic substances include one or more of the following:
   culture media, growth factors, differentiation factors, hydrogels, polymers, antibiotics, anti-inflammatory medications, or immunosuppressive medications.

5. The method of claim 1, wherein the dose is from 0.04 micrograms to 32 mg.

6. The method of claim 1, wherein the BMP is recombinantly generated BMP.

7. A method treating human disc disease, comprising:
   providing a slurry of a dose of a recombinantly generated bone morphogenetic protein and a carrier; and
   introducing the slurry into an intervertebral disc.

8. The method of claim 7, further comprising introducing the recombinantly generated bone morphogenetic protein through a percutaneous or laparoscopic procedure.

9. The method of claim 7, further comprising adding one or more therapeutic substances to the dose of a recombinantly generated bone morphogenetic protein.

10. The method of claim 9, wherein the therapeutic substances include one or more of the following:
    culture media, growth factors, differentiation factors, hydrogels, polymers, antibiotics, anti-inflammatory medications, or immunosuppressive medications.

11. The method of claim 7, wherein the dose is from 0.04 micrograms to 32 mg.

12. A method treating human disc disease, comprising:
    providing a sponge carrier and a dose of a bone morphogenetic protein in contact with the sponge carrier; and
    adhering the sponge carrier to the outside of an existing intervertebral disc annulus.

13. The method of claim 12, wherein the bone morphogenetic protein is recombinantly generated bone morphogenetic protein.

14. The method of claim 12, further comprising adding one or more therapeutic substances to the dose of a bone morphogenetic protein in contact with the sponge carrier.

* * * * *